(12) United States Patent
Heuft et al.

(10) Patent No.: US 6,239,869 B1
(45) Date of Patent: May 29, 2001

(54) DEVICE FOR DETECTING DIFFUSELY SCATTERED IMPURITIES IN TRANSPARENT RECEPTACLES

(75) Inventors: Bernhard Heuft, Burgbrohl; Christoph Roesel, Bonn-Bad Godesberg; Bernd Schoening, Niederzissen, all of (DE)

(73) Assignee: Heuft Systemtechnik GmbH, Burgbrohl (DE)

( * ) Notice: Subject to any disclaimer, the term of this patent is extended or adjusted under 35 U.S.C. 154(b) by 0 days.

(21) Appl. No.: 09/402,685

(22) PCT Filed: Sep. 4, 1998

(86) PCT No.: PCT/EP98/02075

§ 371 Date: Oct. 7, 1999

§ 102(e) Date: Oct. 7, 1999

(87) PCT Pub. No.: WO98/45690

PCT Pub. Date: Oct. 15, 1998

(30) Foreign Application Priority Data

Apr. 10, 1997 (DE) .......................................... 297 06 425 U

(51) Int. Cl.[7] .................................................. G01N 21/00
(52) U.S. Cl. ........................................................ 356/239.5
(58) Field of Search ............................. 356/237.1, 239.1, 356/239.2, 239.4, 239.5, 239.6, 239.7, 239.8, 240.1, 237.2, 237.3; 250/223 B; 382/141, 142

(56) References Cited

U.S. PATENT DOCUMENTS

| | | | | |
|---|---|---|---|---|
| 3,830,969 | * | 8/1974 | Hofstein | 178/6.8 |
| 3,894,806 | * | 7/1975 | Remy et al. | 356/240 |
| 4,249,075 | * | 2/1981 | Lovalenti | 250/223 B |
| 4,459,023 | | 7/1984 | Reich et al. | 356/237 |
| 4,943,713 | * | 7/1990 | Yoshida | 250/223 B |
| 5,134,278 | * | 7/1992 | Nelen | 250/223 B |
| 5,229,837 | * | 7/1993 | Osakada | 356/240.1 |
| 5,258,611 | * | 11/1993 | Leser | 250/223 B |
| 5,528,036 | * | 6/1996 | Achter et al. | 250/339.12 |

FOREIGN PATENT DOCUMENTS

| | | | |
|---|---|---|---|
| 24 62 697 C2 | 7/1980 | (DE) | G01D/21/04 |
| 32 45 908 A1 | 6/1984 | (DE) | B07C/5/342 |
| 42 00 971 A1 | 7/1993 | (DE) | B07C/5/342 |
| 43 00 169 A1 | 7/1994 | (DE) | G01N/21/90 |
| 43 29 047 A1 | 3/1995 | (DE) | G01M/11/00 |
| 43 40 668 A1 | 8/1995 | (DE) | G01N/21/90 |
| 295 02 708 U1 | 5/1996 | (DE) | G01N/21/90 |
| 0429086 A1 | 5/1991 | (EP) | G01N/21/90 |
| 0715166 A1 | 9/1995 | (EP) | G01N/21/90 |
| 02114158 | 4/1990 | (JP) | G01N/21/90 |
| WO 95/22756 | 8/1995 | (WO) | G01N/21/25 |
| WO 97/14956 | 4/1997 | (WO) | G01N/21/90 |

* cited by examiner

Primary Examiner—Frank G. Font
Assistant Examiner—Michael P. Stafira
(74) Attorney, Agent, or Firm—Gardner, Carton & Douglas

(57) ABSTRACT

The device for the detection of diffusely scattering impurities (18) in containers (10) that have a transparent wall (16) has a light source (12), which produces one or more light beams (14) for illuminating the wall (16), and an optical detecting device (22) for production of an image of the illuminated wall (16), with the light source (12) and the optical detecting device (22) arranged according to darkfield detection. The light source (12) is designed so that the light beam or beams (14) that it emits have an intensity distribution over their cross-section with an intensity contrast at one point at least within their cross-section.

12 Claims, 2 Drawing Sheets

DEVICE FOR DETECTING DIFFUSELY SCATTERED IMPURITIES IN TRANSPARENT RECEPTACLES

BACKGROUND OF THE INVENTION

The invention relates to a device for detecting diffusely scattering impurities in containers that have a transparent wall. The containers are illuminated by the dark-field method and are investigated for impurities by means of an optical detecting apparatus.

FIELD OF THE INVENTION

Homogeneous, structureless impurities in transparent containers, e.g. glass bottles, are very difficult to detect by existing methods of investigation. Examples of impurities are, in particular, residues of emulsion paints, rust, minerals and other semitransparent substances. If the containers are illuminated by the bright-field method, it is scarcely possible to detect the structureless impurities, as they merely cause a fluctuation in the transmission behaviour. There are neither changes in contrast nor a sufficiently pronounced decrease in image brightness, as the mean scattering angle is at times only very small. Using an optical detecting device, such as a CCD camera, it is therefore not possible for such impurities to be detected reliably, even if additional methods of image processing, e.g. contrast intensification, are employed.

The dark-field method known from EP-A-0 429 086 is used in particular for detecting transparent plastics films, for example cigarette packaging, in glass bottles. Scraps of plastics film are detected by the optical detecting device (CCD camera with polarizing filter) as image elements with strong contrast, at least in places. Homogeneous, structureless impurities, such as residues of emulsion paints, however, under dark-field illumination only produce image elements that are themselves also structureless and without contrast. The intensity of the light received by the optical detecting device does indeed increase with the scattering power of the impurities, i.e. with the layer thickness, provided absorption effects do not predominate. The increase in intensity of the amount of scattered light detected by the optical detecting device therefore becomes greater relative to containers that are free from impurities, depending on the layer thickness of the impurity. Detection of homogeneous, structureless impurities therefore requires measurement of the absolute intensity. However, experience has shown that with detecting devices there is considerable uncertainty in such measurements.

SUMMARY OF THE INVENTION

The basic aim of the invention is to make it possible for homogeneous, structureless, diffusely scattering impurities to be detected reliably in containers with a transparent wall.

According to the invention this aim is achieved in that the light beam or beams of the light source have a spatial intensity distribution with a contrast in an intensity at one point at least within their cross-section.

This one point, at least, where there is an intensity contrast, is generally the lateral boundary of the cross-section of a light beam. This assumes that the diameter of the light beam is much smaller than the container wall that is to be examined. It is sufficient if the intensity contrast along the light beam is present at the point where the wall to be investigated is located. Preferably, therefore, the light beam is focused on the transparent wall of the container.

It is also possible to use a beam of parallel, converging or diverging light rays or some other kind of illumination, which produce a high-contrast bright/dark distribution of intensity in the wall on which any impurities present are to be detected. In particular, highly collimated light beams such as laser beams are suitable for illumination. It is, preferable to use a chequered or matrix-like arrangement of point light sources or a striped light pattern. It is also possible to produce a sharp image on the container wall of a pinhole diaphragm or slit aperture, which is located at the light source. It is also possible to scan the wall of the container with a scanner. Since homogeneous, diffusely scattering impurities arise for example through large-area evaporation of a solvent—in the beverage industry, as a rule this is water—the contrast pattern can be scanned alt several points that are some distance apart. This greatly improves the reliability of detection of impurities in the form of large-area deposits. The distance between the individual contrast points or light points is then preferably much smaller than the anticipated extent of the deposit.

If no impurity is present on the transparent wall, the light beams pass essentially in a straight line through the wall and, because of the dark-field arrangement, they go past the optical detecting device. If, on the other hand, there is a diffusely scattering impurity on the transparent wall, e.g. a thin film of emulsion paint, the light beam is scattered by the impurity, so that some of the light is received by the optical detecting device. On account of the intensity contrast of the light beam within the transparent wall, the image picked up by the optical detecting device also contains at least one place with a high intensity contrast. This place with high intensity contrast can be detected very reliably, largely independently of the level of the absolute intensity value.

The detecting device according to the invention can also be equipped with a single light source and two or more optical detecting devices. The light source can for example emit several light rays and be arranged so that some of the light rays impinge on the bottom surface of the bottle, whereas others impinge on the side wall. It is then possible to use two CCD cameras, one inspecting via the mouth of the bottle through the bottom, whereas another laterally arranged CCD camera inspects the side wall of the glass bottle. Basically it is possible to operate both with one or more light sources and with one or more optical detecting devices.

The contrast structures detected by the optical detecting device can be brought out clearly by standard image-processing techniques for intensifying contours or contrast, so that reliable distinction between containers with impurities and those without impurities is possible. Due to the sensitivity of the method, even very slight deposits can be detected. For the detection of large-area homogeneous deposits it is therefore sufficient in principle to have a single light beam and therefore a single light spot in the transparent wall, and it is only necessary for instance to check the impingement point of the light spot.

When inspecting a large number of identical glass bottles, which inevitably have an identically shaped bottom of the bottle, the bright spot or spots of lights always appear at the same place, so that these places are examined selectively for the detection of structureless, homogeneous impurities.

In plants that operate with dark-field illumination for detecting structured defects (cracks, flaws in glass, polarization-altering defects, e.g. plastics films), the device according to the invention can be inexpensively installed, by using a source of illumination that has a pattern of high-contrast in the intensity distribution in the transparent wall. The image signals produced can be investigated for the presence of diffusely scattering defects or impurities with the same optical detecting device (CCD camera) that is used for the detection of structured defects. The same measurement principle can also be employed for checking diffusely scattering surfaces (etched or sandblasted surfaces) of otherwise transparent walls and for distinguishing between diffusely scattering surfaces and clear surfaces.

The device according to the invention can also be combined with a device operating according to the bright-field principle. Especially when inspecting the side wall of glass bottles, operation is generally based on the bright-field principle, i.e. the glass bottles pass in front of a large-area light source and are examined for the presence of foreign bodies using a CCD camera. Such an inspection device, working exclusively according to the bright-field principle, is unable to detect diffusely scattering impurities. If, however, a light source is additionally installed according to the dark-field technique, i.e. is set up laterally in front of or behind the glass bottles or other transparent containers that are to be examined, and is aligned so that its rays do not impinge on the CCD camera in the case of containers without diffusely scattering impurities, but are also partly scattered into the CCD camera in the case of containers with diffusely scattering impurities, it is thus possible for diffusely scattering impurities also to be detected at the same time. It is advisable, however, to set the luminous intensity of the large-area bright-field light source to an intermediate value, at which the CCD camera operates in the dynamic range, so that it can detect the additional increase in intensity that is produced when, for example, a diffusely scattering deposit is present on the inside surface of a glass bottle. If the light source of the device according to the invention is for example a field of several parallel laser beams, then relatively sharply delimited points of increased light intensity can be detected on the image produced by the CCD camera, within surroundings of medium light intensity.

The invention is explained in more detail below, on the basis of the drawing, wherein:

DETAILED DESCRIPTION OF THE INVENTION

Figure 1:
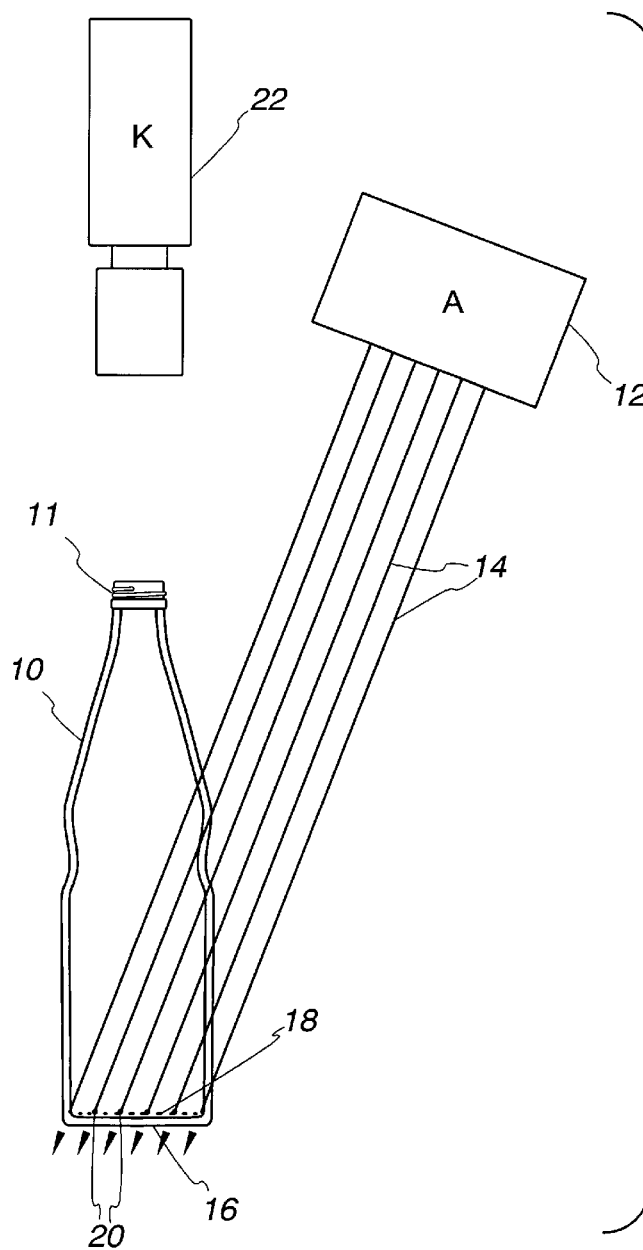
FIG. 1 shows a device for the detection of diffusely scattering impurities in glass bottles.
Figure 2:
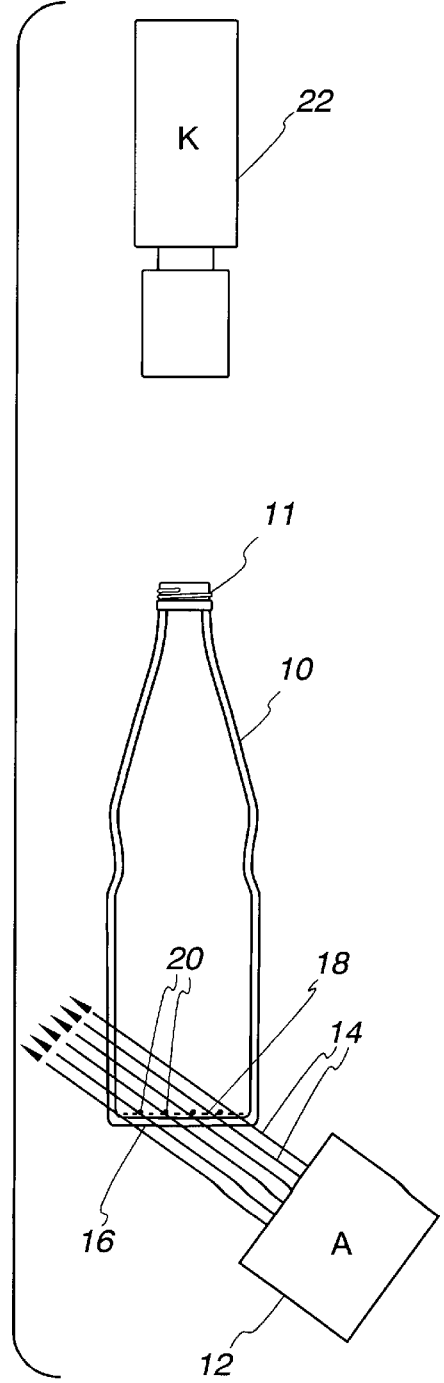
FIG. 2 shows another arrangement of the light source opposite the bottle to be inspected.

In each of FIGS. 1 and 2, a glass bottle 10 with a mouth 11 is transported by means of a conveyor (not shown). This conveyor can be of a kind that is known from EP-A-0 124 164, in which elastic fingers grip below the bead or collar of glass bottles, so that the bottles are suspended and are transported without resting on the bottom of the bottle. If it is only the bottom of the bottle that is to be examined for impurities, it is also possible to use a conveyor of the design known from EP-A-0 163 330, on which the glass bottles are supported by laterally-gripping transporting belts, again without resting on the bottom of the bottle. With these kinds of conveyors, no disturbing reflections occur, such as can occur with a chain-link-chain conveyor, on which the glass bottles are normally transported in the upright position.

A light source 12 directs several finely-collimated light beams 14 with a diameter of a few millimeters, obliquely from above in FIG. 1 and obliquely from below in FIG. 2, onto the bottom 16 of the bottle 10, the points of impingement of the light beams 14 in each case being distributed over roughly the whole bottom 16. In the case of light source 12 it is a laser, the beam of which is split by beam splitters into several beams 14 that are parallel to one another.

In the bottom region of glass bottle 10 there is a layer 18 of an homogeneous, structureless impurity. At the places where the beams 14 pass through the impurity layer 18, some of the beams 14 are scattered diffusely, so that bright spots 20 appear on the bottom of the glass bottles 10. Without the impurity layer 18, the beams 14 would pass unhindered through the bottom of the bottles 10, apart from reflections at the surface of the glass.

By means of a CCD camera 22, an image of the bottom of the bottle is obtained through the mouth 11 of the bottles 10. If an impurity layer 18 is present, causing diffuse scattering of the beams, the spots 20 can be seen in the image produced by the CCD camera. Owing to the sharp collimation of the beams 14, spots 20 give a definite intensity contrast to their immediate surroundings on the image, and this can be evaluated using standard methods of image processing. On the other hand, if the bottle bottom 16 is free from impurities, there is no diffuse scattering of radiation, so that it appears dark on the image produced by the CCD camera 22. The light reflected on the surface of the glass of bottom 16 goes past the CCD camera 22 to one side.

In the embodiment in FIG. 2, the bottom is illuminated from below by the light source 12. If an impurity layer 18 is present, diffuse scattering of the beams 14 again give; rise to bright spots in layer 18, which can once again be detected by a CCD camera 22 via the mouth 11 of the bottle 10, for further processing. In the case of illumination from below, it is advisable for the angle of incidence of the beams 14 to be as flat as possible, so as to prevent reflections on the inside wall of bottle 10 from reaching the CCD camera 22.

In equipment for inspection of empty beverage bottles, the CCD camera 22 is anyway present, as it is a component of the apparatus for example for inspection of the bottom or the side wall, e.g. for detecting foreign bodies in the bottom region or defects in the side wall region of the glass bottle 10. It is therefore sufficient to add the light source 12, in order to adapt existing equipment so that it can also detect dried-on films of emulsion paint residues, rust, minerals and other semitransparent, diffusely scattering materials.

Figure 3:
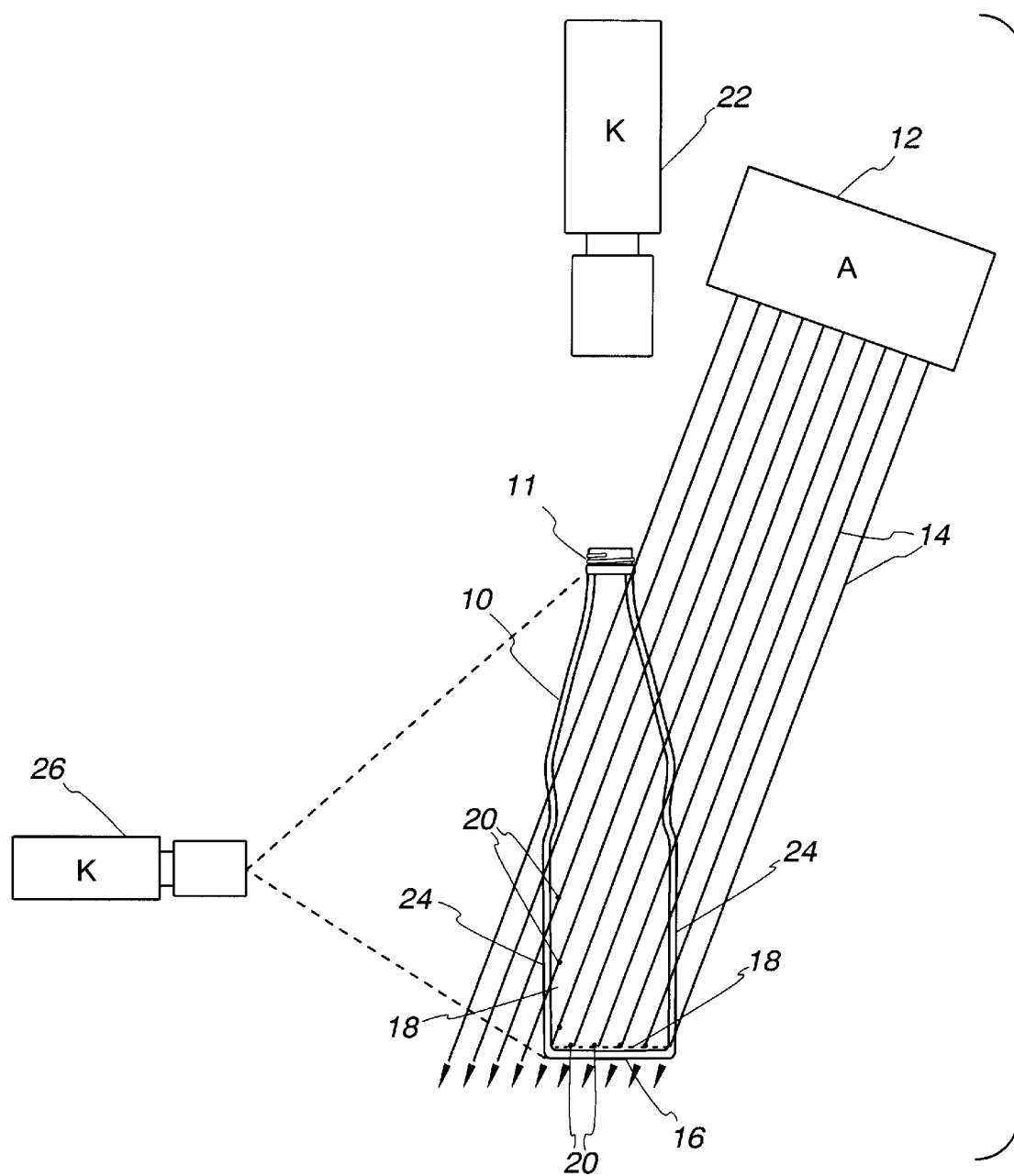
FIG. 3 shows a device for detecting diffusely scattering impurities in glass bottles, which has one light source and two optical detecting devices.

FIG. 3 shows yet another embodiment, similar to FIG. 1, where the light source 12 emits a larger number of light beams 14 and these light beams 14 are distributed over a larger region, so that the light beams 14 impinge not only on the whole bottom 16, but also on the side walls 24. A second CCD camera 26 is arranged laterally next to the glass bottle 10 for the purpose of detecting diffusely scattering impurities on the side walls 24 of the bottle 10. The light beams 14 are then strongly collimated, so that they produce a pronounced intensity contrast in any diffusely scattering impurities that might be present, in both side walls 24 of bottle 10.

What is claimed is:

1. A device for detecting diffusely scattering impurities in containers which have a transparent wall, the device comprising:

a light source for illuminating said transparent wall, said light source comprised of at least one light beam, said at least one light beam having an intensity distribution over its cross-section with at least one intensity contrast point within said cross-section and at least one intensity contrast point impinging upon an area of said transparent wall; and an optical detecting device for producing an image of said transparent wall and for examining, for intensity contrast, said point on said transparent wall where said intensity contrast occurs;

said light source and said optical detecting device being arranged for a dark-field detection.

2. The device according to claim 1 wherein said light source is a laser.

3. The device according to claim 1 wherein said at least one light beam is focused on said transparent wall.

4. The device according to claim 1 wherein a further light source is arranged for bright-field detection, which further light source produces a light beam of larger diameter and more uniform intensity.

5. The device according to claim 1 wherein said at least one light source directs a light beam onto plural walls of said transparent container, which walls are at an angle to one another, and further comprising plural optical detecting devices, which are each being directed onto one of said walls.

6. The device according to claim 1 wherein said light source emits several beams.

7. A device for detecting diffusely scattering impurities in containers which have a transparent wall, the device comprising:

a light source for emitting at least one light beam for illuminating said transparent wall, said at least one light beam having a cross-section and an intensity distribution over said cross-section with an intensity contrast at least at one point within said cross-section and said light source being constructed such that said at least one intensity contrast point of the light beam impinges on an area of said transparent wall;

an optical detection device for producing an image of said transparent wall and for examining, for intensity contrast, said area on said transparent wall where said intensity contrast point of the light beam impinges;

said light source and said optical detecting device being arranged for a dark-field detection; and wherein the light beam is scattered by a diffusely scattering impurity on the transparent wall such that a portion of the light is received by the optical detecting device and wherein the image produced by the optical detecting device also contains an intensity contrast enabling the diffusely scattering impurity to be detected reliably and largely independent of an absolute intensity value of the light beam.

8. The device according to claim 7 wherein said light source is a laser.

9. The device according to claim 7 wherein said at least one light beam is focused on said transparent wall.

10. The device according to claim 7 wherein a further light source is arranged for bright-field detection, which further light source produces a light beam of larger diameter and more uniform intensity.

11. The device according to claim 7 wherein said at least one light source directs a light beam onto plural walls of said transparent container, which walls are at an angle to one another, and further comprising plural optical detecting devices are provided, which are each being directed onto one of said walls.

12. The device according to claim 7 wherein said light source emits several beams.

* * * * *